United States Patent [19]

Dyson et al.

[11] Patent Number: 4,889,606

[45] Date of Patent: Dec. 26, 1989

[54] ELECTROPHORESIS AND TRANSFER FOR

[75] Inventors: Nicholas J. Dyson, Pinner; David P. Pashby, Abbots Langley; Judith M. Parke, Great Missenden, all of England

[73] Assignee: Amersham International plc, Buckinghamshire, England

[21] Appl. No.: 259,646

[22] Filed: Oct. 19, 1988

[30] Foreign Application Priority Data

Oct. 20, 1987 [GB] United Kingdom ............... 8724528

[51] Int. Cl.$^4$ ..................... G01N 27/28; G01N 27/26
[52] U.S. Cl. ............................ 204/182.8; 204/299 R; 204/301; 204/182.1
[58] Field of Search ............. 204/299 R, 182.8, 182.1, 204/182.9, 180.1, 301

[56] References Cited

U.S. PATENT DOCUMENTS

| 4,589,965 | 5/1986 | Kreisher. | |
|---|---|---|---|
| 4,622,124 | 11/1986 | Kreisher et al. | 204/299 R |
| 4,726,889 | 2/1988 | Love et al. | 204/299 R |

FOREIGN PATENT DOCUMENTS

| 186577 | 7/1986 | European Pat. Off. | 204/299 R |
|---|---|---|---|
| 214692 | 10/1984 | German Democratic Rep. | 204/182.8 |
| 2147609 | 5/1985 | United Kingdom | 204/299 R |
| 2169703 | 7/1986 | United Kingdom. | |
| 8102790 | 10/1981 | World Int. Prop. O. | |

OTHER PUBLICATIONS

Dietzen, G. et al., "A Reliable Method for Recovery of DNA Fragments for Agarose and Acrylamide Gels" Analytical Biochemistry 112 (1981), pp. 295–298.

Primary Examiner—John F. Niebling
Assistant Examiner—John S. Starsiak, Jr.
Attorney, Agent, or Firm—Wenderoth, Lind & Ponack

[57] ABSTRACT

A method and apparatus for use in biological testing. The apparatus comprises electrophoresis apparatus comprising a tank (1) the interior of which is formed with a raised portion (5) which splits the tank into the two compartments (6,7) containing electrophoresis electrolyte. Electrodes (8) are provided in each compartment. Electrophoresis is carried out through a gel (not shown) supported by a rigid porous plate (11). The gel is cast onto the porous plate with a transfer membrane (not shown) between the porous plate and the gel. Further electrodes (20,21) are mounted below and above the gel respectively. The method of the invention comprises a first stage using the electric field produced by the electrodes (8) to draw the samples through the gel and a second stage using the electric field produced by the electrodes (20,21) to draw the distributed macromolecules onto the transfer membrane.

18 Claims, 2 Drawing Sheets

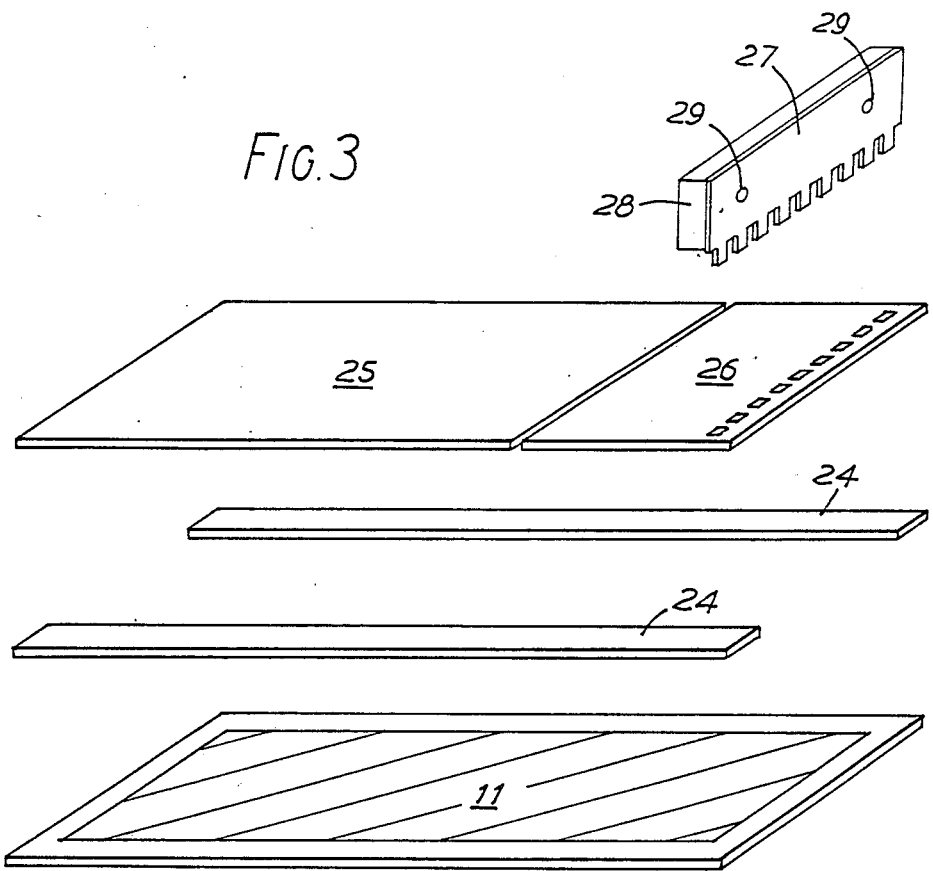
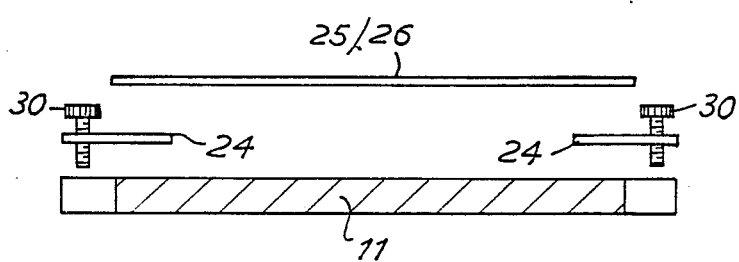

ELECTROPHORESIS AND TRANSFER FOR

This invention relates to a method and apparatus for use in biological testing, in particular in connection with the technique known as "blotting" used to reveal the presence or otherwise of specific macromolecules within suitably prepared samples of DNA, RNA or proteins.

Blotting is the term given to a particular technique for the transfer of DNA, RNA or proteins from a separation gel to a solid support, usually in the form of a membrane. The macromolecules are separated out from the prepared sample by electrophoresis, in which an electric current is used to separate fragments within the sample and distribute them within the separation gel at different spaced positions on the basis of their length or size.

A method for transfer of DNA from an agarose gel to a nitrocellulose membrane was described by Southern (1975) and is now called "Southern blotting". The extension of this approach to transfers of RNA ("Northern blotting" Alwine et al., 1979) and proteins ("Western blotting" Towbin et al., 1979) is well established.

The method described by Southern (1975) relies on capillary diffusion of a salt solution through an agarose gel and nitrocellulose membrane into a stack of absorbant paper, in order to transfer DNA from the gel to the nitrocellulose, and thus produce a replica of the pattern of DNA fragments in the gel on the nitrocellulose membrane. A probe, suitably-labelled, e.g. with radioactivity, specific to the nucleic acid sequence under investigation, is then hybridised to the DNA on the nitrocellulose membrane. The probe will bind to those fragments which contain complementary sequences, and subsequent autoradiography of the nitrocellulose membrane will thus reveal the pattern of bands representing just those DNA fragments in the original sample which contain the nucleic acid sequence under investigation.

The extensive use of Southern blotting has led to the description of many methods for blotting which are variations of the original Southern method. Nylon membranes (Pall. 1980) or chemically-modified or activated papers (e.g. Noyes and Stark, 1975; Seed, 1982) may be used to retain DNA or RNA in place of nitrocellulose. A wide range of transfer solvents have been used in place of the original sodium chloride/sodium citrate solution ($10 \times$ SSC), for example sodium hydroxide (Reed and Mann 1985), ammonium acetate (Smith and Summers, 1980) or phosphate buffer.

The capillary diffusion transfer of DNA can be assisted by application of a vacuum to draw the solvent through the gel and transfer membrane (Peferoen et al., 1982), or by application of a heavy weight to force the solvent through.

Transfer of macromolecules from a separating gel to a membrane can also be accelerated using electrophoretic blotting. A suitably treated gel containing separated macromolecules is put in contact with a membrane and placed between electrodes such that the applied electric current is at 90° to the original direction of separation and the macromolecules are transferred to the membrane maintaining the pattern obtained in the original separation.

Electrophoretic blotting, (also termed electrophoretic transfer or electroblotting) is the most commonly used means of transferring proteins from a gel onto a membrane. Transfer for this technique is far more efficient than diffusion or capillary methods and less diffusion of bands occurs. Electrophoretic blotting of proteins is possible because proteins will bind to nitrocellulose in solutions of low ionic strength. Nucleic acids are only bound to nitrocellulose under conditions which would lead to high electrical currents and therefore overheating, however DNA can be electroblotted onto derivatised nitrocellulose or nylon membranes under low salt conditions. Apparatus and methods for electroblotting are commercially available. Electroblotting, as it is currently used, has several disadvantagous features. Separate pieces of apparatus are required for the initial separation by electrophoresis, and for the subsequent transfer by electrophoresis; the process of preparing and mounting the gel after electrophoretic separation is inconvenient, being a relatively skilled and labour intensive operation. In the case of nucleic acids, preparation of the gel takes 2 to 3 hours and involves depurination and denaturation of the DNA by gel treatment and finally gel equilibration in a transfer buffer. For both protein and nucleic acid electrotransfer the gel has to be placed in intimate contact with a filter membrane ensuring an even contact and that all air bubbles are excluded. Such an even contact is easily achieved by the experienced experimenter but is difficult to automate.

The present invention seeks to remove the need for handling or preparation of the gel between electrophoretic separation and electrophoretic transfer of macromolecules.

In the method of this invention, macromolecules contained in a sample are firstly separated by electrophoresis, then secondly transferred by electrophoresis onto a membrane without treatment or movement of the gel or membrane. Preferably the gel is cast onto the membrane prior to electrophoretic separation, although pre-cast gels may be used. In an embodiment of the invention separation and transfer of the macromolecules can be accomplished in a single buffer. In a further embodiment of the invention separation and transfer of DNA is carried out with double stranded DNA which may be denatured on the membrane after transfer.

In the case of DNA, this may be pretreated with one or more restriction enzymes in order to cut the DNA into different-length fragments which are then separated on the basis of size by the first stage of electrophoresis.

The result of this invention is that the entire gel electrophoresis and blotting process can be performed without movement of the transfer membrane or gel, or without change of solution, merely by sequentially connecting two pairs of electrodes. It will be clear that automation of the blotting is facilitated by the invention and may be accomplished by the addition of an electronic timer and switch device.

The invention also provides equipment for carrying out the method of the invention; said equipment comprising means for mounting a sandwich structure comprising said membrane and gel, first electrode means for applying a first electric current in a first direction operable to separate macromolecules contained in a sample within the gel, and second electrode means for applying a second electric current in a second direction transverse to the first direction for transferring the separated macromolecules within the gel onto the membrane. Preferably said second direction is substantially at right angles to the plane of the first.

In an embodiment of the invention the sandwich structure is supported by a rigid plate of porous material which supports that face of the sandwich structure which comprises the membrane. The use of such a rigid plate enables the membrane to be placed on top of the plate, and the gel directly cast onto it, being confined around the edges by suitable walls. The gel/membrane sandwich structure may be oriented vertically, but in one particular form of the apparatus, to be described below, the rigid porous plate is generally horizontal in use and forms the bottom of a shallow tray onto which the membrane is first placed prior to casting of the gel into the tray. The tray is then immersed in a suitable buffer solution in order to carry out the two-stage electrophoresis operation.

In use of such apparatus, means are provided for first energising the first electrode means to apply said first current to separate the different-length fragments within a suitably prepared sample, usually contained in a well situated at one side of the gel, into the gel and to separate them within the gel according to their size. When the first stage has been completed, the first current is switched off, and the second electrode means energised to apply the second current to carry the fragments in the gel from the gel to the membrane where they locate to thereby reproduce on the membrane the pattern of fragments on the gel.

The electrodes used for electrophoresis may take the form of a plate, or a single wire, or plurality of wires or a grid of wires made, for example, of platinum.

The rigid porous plate needs to be electroporous although it may be advantageous if it has a honeycomb structure in order to avoid distortion to the electric field. This is discussed in more detail below. It may prove even more advantageous if the porous plate is impermeable to large molecules since this would prevent any losses of sample through the sides of the gel.

In an embodiment of the invention, a second one of said rigid porous plates is provided, lying parallel to the first plate, but on the opposite side of the gel/membrane sandwich structure. This second plate, which is removable, may be used to hold the gel and membrane in close contact and can be used for supporting the electrode and for spacing the electrode from the gel. Both rigid porous plates may be of a disposable nature.

The filter membrane may be made from any suitable porous material, for example nylon for nucleic acids and nitrocellulose for protein.

As mentioned above, the gel may be provided in precast form, or may be cast in situ, which latter method has a number of advantages. Casting of agarose gels is straightforward; however, casting of polyacrylamide gels (used for protein electrophoresis) needs a different approach. One problem is that polyacrylamide gels tend to penetrate the pores of the membrane and can therefore be difficult to remove after transfer. This problem can be overcome by incorporating an extra membrane, for example of cellulose triacetate between the gel and the membrane. This has the effect of stopping the polyacrylamide from getting through during casting, but does not interfere with the subsequent separation or transfer. In an alternative arrangement, the gel is laid directly on its porous support plate and the membrane applied to the opposite surface of the gel, instead of being sandwiched between the lower porous plate and the gel. In this case, the separated macromolecules within the gel are transferred in the opposite direction away from the lower porous plate, rather than towards it.

In order that the invention may be better understood, two embodiments thereof will now be described by way of example only and with reference to the accompanying drawings in which:

FIG. 3 is a diagrammatic exploded view of a system which may be used for casting polyacrylamide gels in the presence of a transfer membrane;

FIG. 4 is a diagrammatic end view of the components of FIG. 3; and

FIG. 5 is a diagrammatic perspective view of one example of the electrode structure suitable for electrophoretic transfer.

Figure 1:
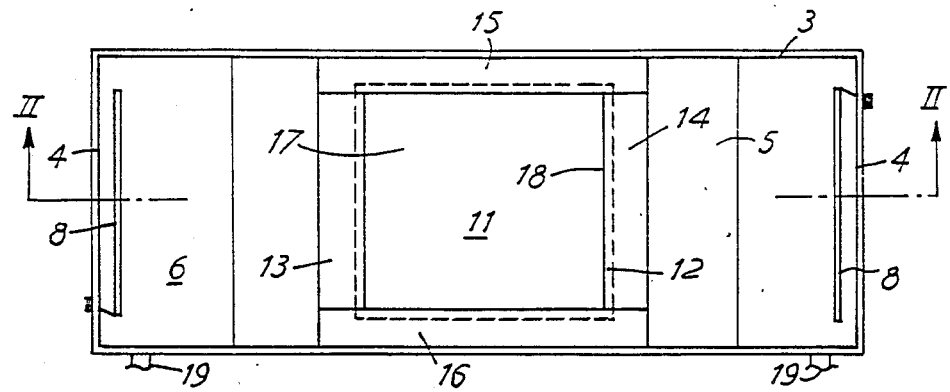
FIG. 1 is a diagrammatic plane view of an electrophoresis apparatus incorporating the equipment of the present invention without the top transfer electrode in place.
Figure 2:
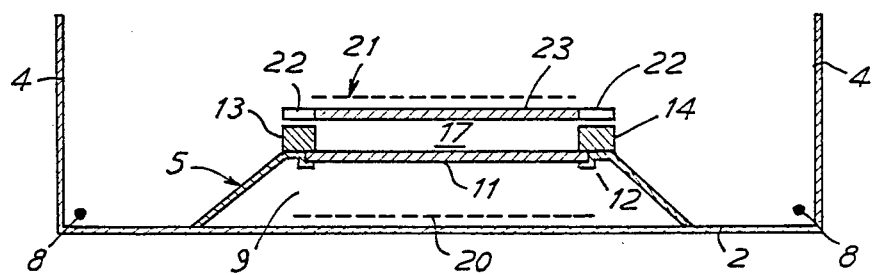
FIG. 2 is a diagrammatic side sectional view of the apparatus along lines II—II of FIG. 1 with the top transfer electrode in place.

Referring to the drawings, the electrophoresis apparatus comprises a generally rectangular tank 1 made of perspex. The tank has a bottom 2, side walls 3 and end walls 4. The central part of the interior of the tank is formed with a raised portion 5 extending right across the width of the tank to thereby split the tank into two compartments 6, 7 which form respective reservoirs for the electrophoresis electrolyte. A platinum electrode 8 is provided in each tank for electrophoretic separation, the electrodes being connected by way of respective terminals (not shown) to exterior circuitry (also not shown).

The raised portion 5 forms with the bottom 2 of the tank a lower chamber 9 which contains a platinum electrode 20 for electrophoretic transfer fixed on the bottom 2 and connected by way of a terminal to exterior circuitry (not shown). The top surface of the raised portion which, in use of the apparatus, is horizontal as shown, is made from a rigid plate 11 of porous material. The plate is supported on suitable flanges 12 to provide a reasonably liquid-tight connection. Four perspex blocks 13 to 16 are placed around the plate, and slightly overlap the edges of same, as shown. These blocks together define a shallow tray 17 having the plate as its bottom. The blocks may be secured in place by any suitable means, such as bolts, but should be readily removable to allow assembly of the components, as will become clear.

In an alternative construction (not shown) the blocks 13–16 are replaced by a rectangle of perspex which has the ends, equivalent to positions occupied by blocks 13 and 14, drilled through with small sloping holes, the holes being highest at the outer edge i.e. the edge facing the electrodes 8. These holes allow passage of current and also permit the rectangle of perspex to remain in place thus increasing the convenience of the system. These blocks or the rectangle of perspex are suitable for the casting of agarose gels but are not ideal for commonly used polyacrylamide gels. A system which would be better suited for polyacrylamide gels and can be incorporated in the equipment design can be seen in FIGS. 3 and 4, and will be described later.

A second platinum electrode 21 used for electrophoretic transfer is mounted on the surface of a second porous plate 23 which is set into a perspex frame 22. This electrode, which need not be present during electrophoretic separation is connected via a terminal to exterior circuitry (not shown). In the apparatus shown, the electrode 21 is shown separated from the plate 23, for clarity; however although we are currently supporting the electrode 21 directly on the plate 23, we envisage that there may be value in raising the electrode 21 above the top of the plate.

In order to use the apparatus for nucleic acid gels the blocks 13-16 are first removed and a suitable transfer membrane (not shown) laid on top of the porous plate. The membrane, if provided with suitable holes, may be located on studs (not shown) used for the attachment of the blocks. The membrane should cover substantially the whole surface of the plate, and certainly that part exposed beyond the blocks.

A layer of suitable electrophoresis gel may be laid on top of the membrane and the blocks 15, 16 then replaced; however, a better method, which is certainly usable with agarose gels, is to replace all the blocks after placement of the membrane, and then cast the gel in the form of a liquid directly onto the membrane, using the blocks to confine the liquid. The agarose gel sets in contact with air to form an intimate membrane/gel interface free of bubbles which may be readily separated when necessary.

During casting of the gel, a multi-tooth comb (not shown) is suspended into the tray 17 to thus define a line of wells close to one end, say end 18 of the tray. After removal of the comb, the wells take the form of cup-shaped depressions which open into the top surface of the gel, and are used for applying the sample or samples under test. This technique is well known in the art and will not be described further.

After setting up the apparatus in this way, electrophoresis may be commenced by filling the two compartments 6, 7 with an electrophoresis electrolyte and connecting the electrodes 8 to a suitable power supply. The compartments are filled up to a level just above the top surface of the blocks, so that the two reservoirs are in fact in liquid communication via a thin layer of liquid above the raised portion 5. A sample or samples are introduced into the wells formed in the top surface of the gel and the separation electrophoresis commenced by applying a potential across the separation electrodes 8. If blocks 13,14 are in place at this time, they should be removed prior to the commencement of the electrophoresis; likewise the frame 22 and electrode 21.

When separation electrophoresis is complete, the power supply is removed from the separation electrodes 8, the perspex blocks 13 and 14 are replaced and the transfer structure comprising electrode 21, frame 22 and plate 23 is placed in position on top of blocks 13-16.

Before commencing electrophoretic transfer it is necessary to ensure that the electrophoresis electrolyte is above the electrode 21. The power supply is connected to the transfer electrodes 20,21 so that the negatively charged macromolecules migrate through the gel towards the anode 20 and are retained on the membrane in a pattern which corresponds to that in the gel. Electrophoretic transfer is carried out for 15-180 minutes at approximately 200 V or 200 mA. The precise electrophoretic conditions will vary according to the composition, percentage and thickness of the gel although the same variety of conditions are possible as in a conventional commercial electrotransfer apparatus.

After electrotransfer, the perspex blocks 13 to 16, frame 22, porous plate 23 and transfer electrode 21 are removed from the apparatus to enable the membrane/-gel structure to be lifted off. The membrane is now separated from the gel and treated accordingly. In the case of DNA the membrane may be subjected to conditions which denature the DNA on the membrane and render it more accessible for subsequent hybridisation.

Although the system has been shown to work the positioning of electrodes 20, 21 has not been optimised; placing them equidistant from the gel may provide a slight increase in resolution.

There will now be described an example of the use of this apparatus for the separation and transfer of nucleic acids.

The action of electrophoresis is well documented and will not be described here in detail. Generally speaking the DNA samples introduced into the wells will have been subjected to an initial stage in which the DNA is cut by reaction with one or more restriction enzymes to form different-length fragments. The action of the electrophoresis is to separate these fragments, on the basis of their size, into a pattern of bands which migrate along the gel towards the anode.

Denaturation of DNA on nylon or nitrocellulose membranes is achieved by soaking the membrane in an alkaline solution. Using DNA blotted to Hybond N, 5-10 minutes soaking in 0.5M NaOH, 1.5M NaCl is optimal although improvements in hybridisation performance over double strand DNA is observed after a wide variety of times in a range of alkali and salt conditions. The alkali is neutralised by immersing the filter membrane in 0.5M Tris pH 7.4, 0.9M NaCl for 2-3 minutes.

DNA can be immobilised for hybridisation by air drying, baking or crosslinking by U.V. irradiation according to standard techniques and subjected to the usual hybridisation and autoradiography procedures.

The following sequence describes the steps necessary in the use of the apparatus for the analysis of already-fragmented DNA samples, and the results obtained.

(1) Casting an agarose gel on a nylon transfer membrane

A Hybond TM N nylon membrane (pore size 0.45 $\mu$m from Amersham International) was cut to size and placed in position over the porous plate 11. The edges of the membrane were sealed by the four perspex blocks 13 to 16 which act as the mould for the sides of the gel (see below).

Agarose (Sigma, Type II) was dissolved to 0.8% in $\frac{1}{2}$×TBE running buffer ($\frac{1}{2}$×TBE is 45 mM Tris-HCl pH 8.3, 45 mM borate, 1.25 mM EDTA) by boiling. The solution was cooled to 65° C. and a 5 mm thick gel cast by pouring the agarose solution gently onto the centre of the dry membrane. The membrane wets as the agarose is poured and forms an even contact with the porous plate-slow pouring of the agarose solution ensures that no air bubbles form between the gel and the membrane nor between the membrane and the plate. Alternatively, the agarose can be poured onto a wet membrane but it is important to ensure that any air bubbles beneath the membrane are carefully removed.

A comb is positioned in the gel such that the bottom of the wells are 2 mm above the nylon membrane. The agarose is allowed to cool to room temperature.

(2) Electrophoretic separation of nucleic acids

The comb is removed from the gel, electrophoresis buffer added ($\frac{1}{2}$×TBE) with bromophenol blue and xylene cyanol or orange G as marker dyes. Perspex blocks 13 and 14 must be removed from the apparatus before the gel can be run. Electrophoresis of DNA was carried out at 1-10 V/cm for 2-16 hours by connecting separation electrodes 8, to a power supply.

(3) Electrophoretic transfer of nucleic acids

When separation of nucleic acids is complete, the power supply is removed from the separation electrodes, and blocks 13, 14 and the structure comprising frame 22, plate 23 and transfer electrode 21, put in place. Power supply is connected to electrodes 20 (anode) and 21 (cathode) and the nucleic acids electrotransferred at 100–200 V; 200 mA for 30 minutes.

(4) Denaturation of DNA on the nylon membrane

Blocks 13–16 and the structure comprising frame 22, plate 23 and electrode 21 are removed from the apparatus to release the gel and membrane. The membrane is separated from the gel and placed on the surface of a solution of 0.5M NaOH, 1.5M NaCl for 10 minutes. The membrane is then placed on the surface of a solution of 1.5M Tris pH 7.4, 0.9M NaCl for 2 minutes.

The membrane is air dried for 20 minutes then cross-linked to the DNA by exposure to U.V. irradiation on an ultra-violet transilluminator (UV wavelength 302–305 nm).

(5) Hybridisation and autoradiography

Blots of DNA were prehybridised and hybridised with probes prepared and used following protocols in Amersham International's rapid hybridisation system RPN 1503.

Filters were washed 4 times for 5 minutes at 65° C. in 2×SSC, 0.1% SDS and twice at 65° C. in 0.2×SSC, 0.1% SDS. Autoradiography was at −70° C. to X-ray film with Cronex Lightening Plus intensifying screens.

Result: Autoradiography of a Southern blot showing single copy gene detection in human DNA after a 16 hour exposure. The result shows the correct single copy band with no background signal and good resolution of the DNA. This is essentially the same result as obtained using standard methods.

The apparatus of the invention can also be used for the electrophoretic separation and transfer of other macro-molecules such as proteins and the separation of nucleic acids on other types of gel e.g. as used in nucleic acid sequencing, although the experimental details may differ from those used when separating and transferring nucleic acids from agarose gels. Urea gels, SDS polyacrylamide gels, lithium dodecyl sulphate containing gels, non-denaturing gels, two-dimensional gels, gradient gels and agarose gels can all be used for electrophoretic separation and blotting of proteins. The most commonly used, and that which has been used with the equipment described here, is polyacrylamide gels. Polyacrylamide gels are generally thinner (less than 4 mm) than agarose gels and normally require the exclusion of atmospheric oxygen, for polymerisation to occur so the gel casting method differs from that already described. In order to be able to use the equipment with standard polyacrylamide gels, pre-cast gels have been used.

FIGS. 3 and 4 show a gel casting system suitable for protein gels. In the system of FIG. 3, the porous plate 11 remains unchanged. Two spacers 24 hold porous plates 25 and 26 a fixed distance above the porous plate 11. These spacers 24 could be supplied in a variety of thicknesses allowing different capacity and types of gels to be used. The transfer membrane (not shown) is held in position between the spacers 24 and trapped against the porous plate 11. The spacers 24 clamp down onto the transfer membrane by means of fixing screws 30. The components 11, 24, 25, 26 and 30 (including the transfer membrane) are assembled and the polyacrylamide gel solution is added between the transfer membrane and the porous plates 25 and 26. Capillary action draws the gel solution into the space between the transfer membrane and the porous plates 25 and 26. Before the gel has set a well former 27 is slotted into position. The well former 27 can be varied in height by releasing locking screws 29 which are located in a groove in former 27 and screw into a depth stop 28.

By splitting the upper porous plate into separate elements 25, 26 it may be possible to cast two different gel types. For example stacking and separating gel is a commonly used technique. The gel under plate 25 would be the main gel for separating the proteins and is simply referred to as the separating gel. The gel under plate 26 would be of a different composition and would be used to concentrate the protein sample into a discrete band; this gel is usually referred to as the stacking gel.

Other methods for polymerising acrylamide include the incorporation of U.V. activatable cross-linking agents. These may allow the polymerisation process to occur in air so that the above-described method for casting agarose gels may also be applicable to some polyacrylamide gels.

The process of actually using the polyacrylamide gel for electrophoresis generally follows that already described for agarose gels, differences between the two processes being largely due to the choice of buffers used. With the method used by the present applicant (Laemmli, 1970) for the electrophoretic separation of proteins, the electrophoresis buffer used contained 0.19M Glycine, 0.025M Tris, 0.1% SDS. The electrophoretic transfer buffer contained 0.19M Glycine 0.025M Tris, 20% Methanol. It has been shown to be possible to use the separation buffer for the transfer process. The use of methanol has some advantages but it is not strictly necessary (Gershoni and Palade, 1983). The two buffer system can be used but the single buffer system offers advantages in ease of use, time saving and a potential for automation of the separation and transfer process.

The polyacrylamide gel separates proteins on the basis of molecular size, the gel itself having a sieving effect. The proteins are electrophoretically separated and transferred in a similar manner to that described above for nucleic acid gels. Once transfer is complete, the length of time varying according to conditions used, the gel is removed and the membrane can then be used as required. Proteins, once on the membrane, usually nitrocellulose, are normally bound tightly so no additional treatment of the membrane is required.

The protein, once bound to the membrane, can be detected, according to the nature of the sample, by using any of a number of techniques including: direct total protein stain, lectin binding, antibody binding, ligand binding and autoradiography. All of these techniques are well documented.

The following sequence describes the steps necessary in the use of the above-described apparatus for the separation and transfer of proteins in polyacrylamide gels.

(1) Casting a polyacrylamide gel

A gel solution was prepared containing: 9.77% acrylamide, 0.23% bis-acrylamide, 0.37M Tris pH 8.8, 0.035% ammonium persulphate, 0.1% SDS (sodium dodecyl sulphate). To this mixture 60 $\mu$l of TEMED (N, N, N', N'-tetramethylethylenediamine) was added, the solution was mixed and the gel mixture was poured in a sub-cell PAGE casting system (Bio-Rad U.S. Pat. No. 4,246,222). Once the gel had set it was removed from the gel casting apparatus.

A Hybond ™ C nitrocellulose membrane (pore size 0.45 $\mu$m from Amersham International) was cut to size and placed in position over the porous plate 11. The polyacrylamide gel was cut to size and placed on top of the nitrocellulose. Electrophoretic separation buffer (0.19M glycine, 0.025M Tris, 0.1% SDS) was added until compartments 6 and 7 were full and the liquid level was up to the edge of the gel.

(2) Electrophoretic separation of proteins

Protein samples were solubilised in 1% SDS, 0.0025% bromophenol blue, 5% glycerol, 0.1% β-mercaptoethanol, 0.125M Tris pH 6.8 and boiled for two minutes. 10 μl samples were loaded to each well. Electrodes 8 were then connected up to a suitable power supply and separation electrophoresis carried out at 1–5 V/cm for 45 minutes–2 hours.

(3) Electrophoretic transfer of proteins

Once separation of proteins had been completed, the power supply was disconnected from the separation electrodes.

The electrophoretic transfer buffer was then used to fill compartments 6, 7 and chamber 9. The gel, nitrocellulose membrane and porous plate 11 were replaced taking care to avoid trapping any air bubbles. Porous plate 23, frame 22 and electrode 21 were put in position. Electrophoretic transfer buffer was then added to fill the tank. The lid (not shown) of the tank was then replaced in such a manner that pressure was exerted downwards on plate 23, this ensuring that the gel and membrane maintained close contact. The power supply was connected to electrodes 20 (anode) and 21 (cathode) and the proteins electro-transferred at 200 mA for one hour. The current was maintained as constant and the voltage allowed to vary (decreasing from 50 V down).

(4) Detection of electrophoretically transferred samples

After electrophoretic transfer had been completed and structure comprising porous plate 23, frame 22 and electrode 21 was removed. The gel was discarded and the nitrocellulose membrane then rinsed in 5 mM Tris pH 7.6, 137 mM sodium chloride, 0.1% Tween TM −20. The protein samples on the nitrocellulose membrane were visualised using Amersham International's blotting detection kit, RPN 22.

Result: Visualising the proteins with the detection kit showed sensitivity (i.e. efficiency of transfer) which was comparable to using two separate pieces of equipment. Bands of protein were shown in the correct positions with no background signal and good resolution of the protein.

A problem which may be encountered as a result of including the extra electrodes necessary for the two-stage electrophoresis is that of electric field distortion. This problem may be overcome by removing the top transfer electrode 21 (as described above) during electrophoretic separation, and by using porous polyethylene sheets above and below the gel/membrane sandwich structure during electrophoretic transfer. It is believed that the above-referred to honeycomb structure of the porous plate 11 is also important.

An electrode construction intended to minimise field effects is illustrated in FIG. 5. In FIG. 5, the four electrodes, two for separation, two for transfer are given the same reference numerals as hitherto; the gel/membrane sandwich structure is illustrated under reference 31. The upper and lower transfer electrodes each consist of a plurality of parallel wires serially connected via diodes D.

A further method of minimising electric field distortion is to arrange that the upper transfer electrode 21 is fixed in place, but the electrolyte level is kept below it during separation electrophoresis, the level being raised between separation and transfer to bring the electrode into contact. However, it is hoped that, provided the field effects can be overcome, the apparatus may be run with all four electrodes submerged. The use of diodes in the electrode array, as described above, should help. If this is achieved, then the chamber 9 will no longer need to be separated from the remainder of the tank and this would facilitate use of the apparatus and would make the design simpler.

It is a well known phenomenon that gases are produced at electrodes when a current flows through a conducting liquid. It is inevitable that the bubbles will rise and this may be a problem for the bubbles released from the lower electrode 20. These bubbles may accumulate under porous plate 11 and so interfere with the electric field generated thereby creating local areas of low and high field strength. To get round this problem a third porous plate (not shown) could be inserted between the lower electrode 20 and the porous plate 11. This third porous plate could be tilted diagonally so as to deflect the bubbles and transfer them to some non-interfering area whilst itself having no detrimental effect on the electric fields generated.

In the system described and also in almost all (if not all) commercially available systems each electrode wire carries an equal amount of current. By treating each wire of the transfer electrodes 20, 21 as a separate electrode it is possible to bias the current to make the field stronger in some regions (Gershoni et al., 1985). This will be important for electrophoretic transfer since small proteins or nucleic acids migrate faster than larger ones. In effect, with a uniform field, small macromolecules rapidly leave the gel and contact the membrane, and with continued exposure to a current they can pass through the membrane. Large macromolecules need a longer exposure to the current and even then transfer may only be at low efficiency. By biasing the field strength of the electrode array the macromolecules may be more uniformly transferred regardless of size.

The methods described herein have advantages over existing blotting methods in that they combine the following features:

1. Short transfer times; at 15–60 minutes transfer times are similar to those observed in standard protein electroblotting and those claimed for vacuum assisted transfer of nucleic acids.

2. No gel treatments are required between separation and transfer.

3. No handling of gel nor membrane between separation and transfer.

4. Electrophoretic separation and electrophoretic transfer can be carried out in a single buffer.

5. No equipment is required for transfer in addition to the equipment used for separation (i.e. no additional transfer apparatus, powerpack or controlled vacuum source).

6. Full automation of the blotting process is facilitated for reproducibility and convenience.

7. The apparatus and methods can be easily adapted to accommodate transfer of proteins and nucleic acids from both agarose and acrylamide gels.

8. Genomic nucleic acid sequencing can also be carried out using this system.

REFERENCES

Alwine J. C., Kemp D. J., Parker B. A., Resier J., Renart J., Stark G. R. and Wahl G. M. (1979) in Methods in Enzymology, 68, p 220–242, Wu R. (ed) Academic Press Inc., London and New York.

Bers G. and Garfin D. (1985), Biotechniques, 3, p 276–288.

Gershoni J. M., Davis F. E. and Palade G. E. (1985) Anal. Biochem., 144, p 32–40.

Gershoni J. M. and Palade G. E. (1983), Anal. Biochem., 131, , p 1–15.

Noyes B. E. and Stark G. R. (1975), Cell, 5 p 301–310.

Pall D. B. (1980) Colloids Surf. 1, p 235–256.

Peferoen M., Huybrechts R. and De Loof R., (1982) Febs Letts, 145 (2), p 369–372.

Reed K. C. and Mann D. A. (1985) Nucl. Acids Res., 3, p 7207–7221.

Smith G. E. and Summers M. D. (1980) Anal. Biochem, 109, p 123–129.

Southern E. M. (1975) J. Mol. Biol., 98, p 503–517.

Towbin H., Staehelin T. and Gordon J. (1979) Proc. Natl. Acad. Sci., U.S.A., 76,-4350–4354.

We claim:

1. A method for use in biological testing, said method comprising making up a sandwich structure comprising an electrophoresis gel and a membrane subjecting a sample to a first stage of electrophoresis in which macromolecules contained within the sample are drawn out of a reservoir containing the sample by means of a first electric field and are distributed along the electrophoresis gel at spaced positions dependent upon their size and/or charge, thence subjecting the distributed macromolecules within the gel to a second stage of electrophoresis in which the distributed macromolecules are transferred to the membrane by means of a second electric field transverse to the first electric field, and thence separating the membrane and the gel.

2. The method as claimed in claim 1 wherein the electrophoresis gel is cast directly onto the membrane prior to the commencement of the first stage of electrophoresis.

3. The method as claimed in claim 1 in which the membrane and gel are supplied in pre-cast form.

4. The method as claimed in claim 1 wherein the sandwich structure comprises an additional layer of material separating the gel and the membrane.

5. The method as claimed in any one of the preceding claims wherein said electric fields are set up within a common buffer solution which is not changed between the first and second stages of electrophoresis.

6. The method as claimed in claim 1 wherein the first and second electric fields are established by applying an electric potential between a respective pair of electrodes, the method comprising sequentially connecting the appropriate pair of electrodes to establish the first, then the second electric field, as the test proceeds.

7. The method as claimed in claim 1 wherein said first electric field is established in a plane substantially parallel to the plane of the gel, and wherein said second electric field has a direction transverse to that plane.

8. The method as claimed in claim 7 wherein said second electric field is oriented substantially at right angles to said plane.

9. Apparatus for use in biological testing, said apparatus comprising means for mounting a sandwich structure comprising a membrane and an electrophoresis gel, first electrode means for applying a first electric current in a first direction operable to separate macromolecules contained in a sample within the gel, and second electrode means for applying a second electric current in a second direction transverse to the first direction for transferring the separated macromolecules within the gel onto the membrane.

10. Apparatus as claimed in claim 9 wherein said first direction lies in a plane substantially parallel to the plane of the gel, and wherein said second direction is transverse to the plane of the gel.

11. Apparatus as claimed in claim 10 wherein said second direction is substantially at right angles to the plane of the gel.

12. Apparatus as claimed in any one of claims 9 to 11 comprising a plate of electroporous or electroconductive material which is operable to support the sandwich structure which comprises the membrane and gel.

13. Apparatus as claimed in claim 12 wherein said plate forms the bottom of a shallow tray into which the membrane may be first placed prior to casting of the gel into the tray to form said sandwich structure.

14. Apparatus as claimed in claim 12 wherein said plate also functions as an electrode forming part of said second electrode means.

15. Apparatus as claimed in claim 12 comprising a further plate of porous material, said further plate lying parallel to the first-mentioned plate, but on the opposite side of the gel/membrane sandwich structure, and being operable to hold the gel and membrane in close contact.

16. Apparatus as claimed in claim 12 wherein said plate, and said further plate (if fitted), are made from electroporous material.

17. Apparatus as claimed in claim 9 wherein said mounting means comprises a housing incorporating reservoir means for holding a buffer solution in which said electrode means are immersed in order to establish said electric fields.

18. Apparatus as claimed in claim 9 wherein said membrane is made of porous material.

* * * * *